United States Patent [19]

O'Neill

[11] 4,280,511
[45] Jul. 28, 1981

[54] RING ELECTRODE FOR PACING LEAD AND PROCESS OF MAKING SAME

[75] Inventor: Edward G. O'Neill, St. Paul, Minn.

[73] Assignee: Medtronic, Inc., Minneapolis, Minn.

[21] Appl. No.: 124,156

[22] Filed: Feb. 25, 1980

[51] Int. Cl.³ ............................................. A61N 1/04
[52] U.S. Cl. ................................................... 128/784
[58] Field of Search ..................... 128/419 P, 784–788

[56] References Cited

U.S. PATENT DOCUMENTS

| 3,572,344 | 3/1971 | Bolduc | 128/786 |
| 3,769,984 | 11/1973 | Muench | 128/419 P |
| 3,837,347 | 9/1974 | Tower | 128/785 |
| 3,871,382 | 3/1975 | Mann | 128/419 P |
| 4,156,429 | 5/1979 | Amunson | 128/419 P |

Primary Examiner—William E. Kamm
Attorney, Agent, or Firm—John L. Rooney; Lew Schwartz; Joseph F. Breimayer

[57] ABSTRACT

Ring electrode for a pacing lead where the ring electrode is secured to a conductor coil by soft metal disposed in a slit in insulation over the conductor coil. A slit or hole is punched into the insulation before or after the insulation is pulled over the coiled conductor, silver ball or wire or other like soft metal is placed in the slit or hole, a ring is slid over the insulation and centered over the soft metal, and the ring is swaged to the same diameter as the insulation utilizing an internal mandrel in the conductor coil so that the soft metal is pressed between the ring electrode and the coiled conductor resulting in a mechanically crimped joint. The ring electrode provides flexibility within the lead and the insulation extending through the ring electrode. Tensile strength at the ring electrode is substantially equal to that of the insulation. The ring electrode is swaged to the same diameter as the lead body resulting in a smooth surface and providing for easy lead passage.

6 Claims, 3 Drawing Figures

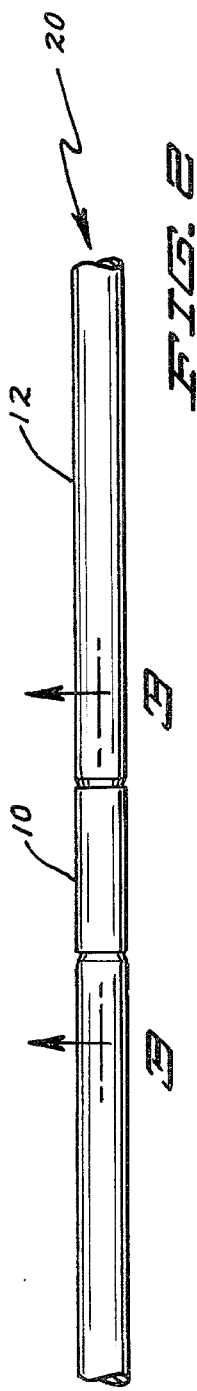
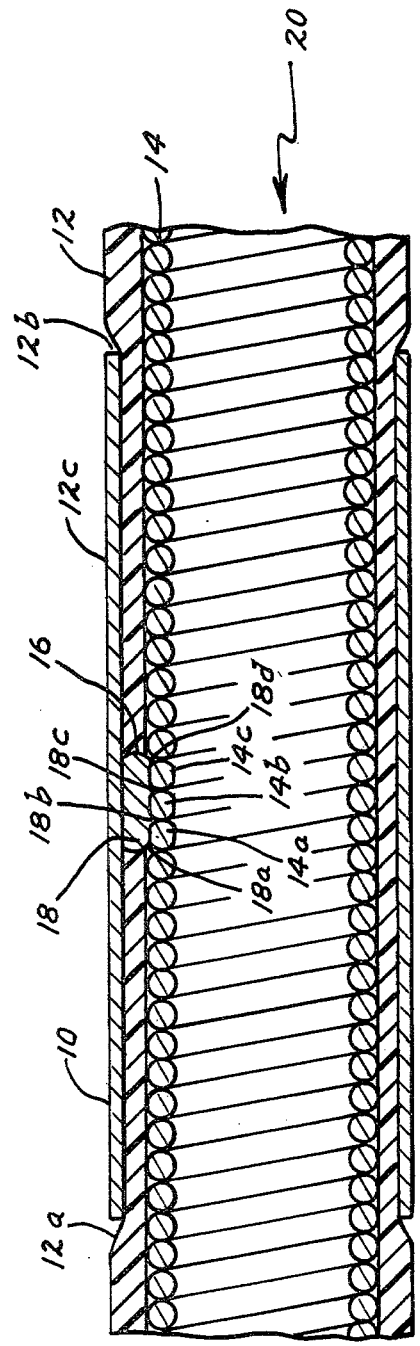
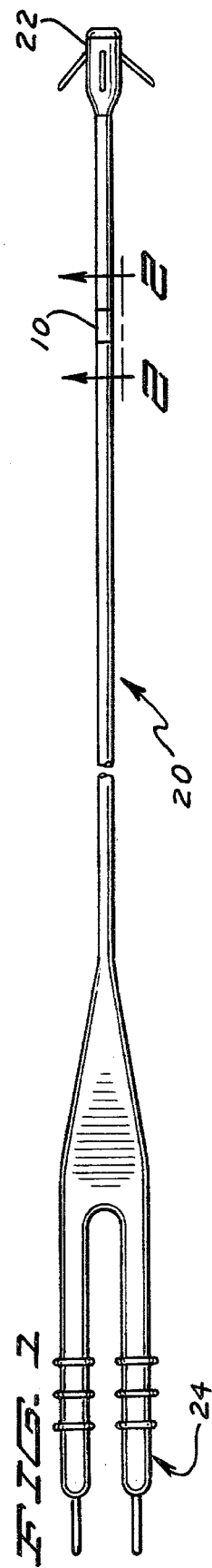

RING ELECTRODE FOR PACING LEAD AND PROCESS OF MAKING SAME

BACKGROUND OF THE INVENTION

1. Field of the Invention

The present invention relates to a surgical electrical applicator, and more importantly, pertains to a ring electrode for pacing lead and process of making same.

2. Description of the Prior Art

Existing types of pacing leads have sometimes presented an uneven surface at the junction of the ring electrode and the insulated coiled conductor of the pacing lead. The tensile strength of the ring electrode at the interface of the insulated coiled conductor is considerably less than desirable. An example is urethane tubing surrounding a ring electrode which changes due to a possible weak interface fit. The interface fit is the weakest portion of the pacing lead and is less than desirable.

The present invention provides that insulation of a pacing lead such as urethane which extends through a ring electrode provides a tensile strength at the ring electrode which is substantially equal to that of the property of the insulation over the coiled conductor.

SUMMARY OF THE INVENTION

The present invention provides a ring electrode and process of making same where the ring electrode secures to insulation of the pacing lead such as urethane providing for the insulation to extend through the ring electrode resulting in tensile strength at the ring electrode substantially equal to that of the insulation.

According to one embodiment of the present invention, there is provided a ring electrode on a pacing lead comprising a coiled conductor, insulation over the coiled conductor, at least one slit in the insulation over the coiled conductor, a soft metal ball or wire inserted and positioned within the slit into engagement with the coiled conductor, and a ring electrode positioned over the soft metal whereby the ring electrode is swaged to the coiled conductor thereby mechanically joining the soft metal which spreads out between the inner surface of the ring electrode and a plurality of turns of the coiled conductor thereby providing for a ring electrode which is the same outer diameter as that of the insulation of the pacing lead and further providing for a smooth outer surface and a tensile strength at the ring electrode substantially equal to that of the insulation of the tubing.

According to another embodiment of the present invention, there is provided a process for affixing a ring electrode at a predetermined location on a pacing lead comprising the steps of providing at least one hole or slit in insulation tubing over the coiled conductor whether the coiled conductor is threaded over the coil or is to be threaded over the coil, inserting at least one soft metal member such as a ball or wire into the hole in the insulation engaging against at least one turn of the coiled conductor, sliding a ring electrode over the insulation and centering the ring electrode over the soft metal, and swaging the ring electrode to the substantially same outer diameter as the insulation whereby the soft metal mechanically joins the ring electrode to the turns of the coiled conductor thereby providing a pacing lead having a ring electrode with the same outer diameter as the insulation of the pacing lead thereby providing a smooth surface and having a tensile strength at the ring electrode which is substantially equal to that of the insulation covering the coiled conductor of the pacing lead.

A significant aspect and feature of the present invention is a pacing lead having a ring electrode which has the same outer diameter as the insulation such as urethane covering the coiled conductor of the pacing lead thereby providing a smooth surface on the outer insulated body of the pacing lead. The smooth outer surface is particularly desirable and provides for easy passage of the pacing lead through veins of the patient's body and lead insertion devices, and further minimizes thrombus formation.

Another significant aspect and feature of the present invention is a ring electrode for pacing lead and a process for making same which offers economic advantages in being easily and readily produceable with little chance for manufacturing defects.

A further significant aspect and feature of the present invention is a pacing lead which is more flexible in the area surrounding the ring electrode than the prior art leads.

Another significant aspect and feature of the present invention is to provide a pacing lead which is easy to pass around curves, especially in veins.

Having thus described one embodiment of the present invention, it is an objective hereof to provide a ring electrode for pacing lead and process for making same, especially for urethane pacing leads, which provides a pacing lead having a ring electrode the same diameter as the lead body, a smooth surface between the ring electrode and the lead body, and offering utmost flexibility at the interface junction of the ring electrode and the pacing lead.

BRIEF DESCRIPTION OF THE DRAWING

Other objects and many of the attendant advantages of this invention will be readily appreciated as the same becomes better understood by reference to the following detailed description when considered in connection with the accompanying drawings, in which like reference numerals designate like parts throughout the FIGURES thereof and wherein:

FIG. 1 illustrates a plan view of a bipolar pacing lead with a ring electrode, the present invention, adjacent to the distal end of a pacing lead;

FIG. 2 illustrates a plan view taken along line 2—2 of FIG. 1 of the ring electrode over the distal section of the pacing lead; and, FIG. 3 illustrates a cross-sectional view taken along line 3—3 of FIG. 2.

DESCRIPTION OF THE PREFERRED EMBODIMENT

FIG. 1, which illustrates a plan view of a bipolar coaxial pacing lead 20, shows a ring electrode 10, the present invention, adjacent the distal end of the pacing lead 20. An electrode 22 is positioned at the distal end of the pacing lead 20 and includes a plurality of tines surrounding the electrode 22 and terminal pins 24 is positioned at the proximal end of the pacing lead 20.

FIG. 2, which illustrates a plan view taken along line 2—2 of FIG. 1 of the ring electrode 10 of the present invention, shows the ring electrode 10 crimped around insulation 12 of the pacing lead 20 which includes the electrode 22 at the distal end as illustrated in FIG. 1, the terminal pins 24 at the proximal end where the pacing electrode and terminal pins 24 are not illustrated in the figure for purposes of clarity in the figure. The outer diameter of the ring electrode 10 is substantially equal to the outer diameter of insulation 12 of the pacing lead 20.

FIG. 3, which illustrates a cross-sectional view taken along line 3—3 of FIG. 2, shows the ring electrode 10 crimped about the pacing lead 20 adjacent the distal end so that the outer diameter of the ring electrode 10 is substantially equal to the outer diameter of the insulation 12 of the pacing lead 20. The inner coaxial, coiled conductor is not illustrated in the figure for purposes of clarity in the figure and accompanying description. The insulation 12 of the pacing lead surrounds a coiled pacing conductor 14 which can be multifilar nickel alloy coiled conductor commonly referred to as MP35N by way of example and for purposes of illustration only and which can be manufactured under the Drawn-Brazed-Stranded (DBS) process. The insulation 12 can be urethane or polyether urethane elastomer as now used for covering coiled conductor 14. A slit 16 is provided in the insulation 12 either before the insulation 12 is pulled over the coiled conductor 14 or afterwards. A ball or wire of soft metal 18 such as silver by way of example and for purposes of illustration only and not to be construed as limiting of the present invention is positioned in the slit 16 and the ring electrode 10 is subsequently crimped mechanically joining the ball or wire of soft metal 18 between the ring electrode 10 and the coiled conductor 14.

During the crimping or swaging process, the ball or wire of soft metal 18 extrudes in between the voids of the coiled conductor forming teats 18a–18d. Also, the coiled conductors 14a–14c tend to somewhat flatten with respect to the other coiled conductors which maintain a circular cross-sectional configuration. Finally, the insulation at points 12a and 12b forms somewhat slight voids and flattens to a width at 12c.

PREFERRED MODE OF OPERATION

The process for securing the ring electrode 10 around the insulation 12 and to the coiled conductor 14 of the pacing lead 20 comprises the steps of first punching or slitting a hole 16 in the insulation 12 of the coiled conductor 14 of the pacing lead 20, either after the insulation 12 is slid over the pacing conductor 14 or prior to the sliding over of the insulation 12 over the pacing conductor 14. A soft metal ball or wire 18 such as silver by way of example and for purposes of illustration only, positions into the slit 16 or if there are a plurality of slits 16, the appropriate balls or wire corresponding in number to the slits are positioned in the slits. The ring 18 is then slid over the insulation 12 and over the ball or wire 18, and centered appropriately as best illustrated in FIG. 2. Subsequently, the ring electrode 10 is swaged at the predetermined locations, possibly with the aid of an internal mandrel having the same internal diameter as the coiled conductor 14, so that the ring electrode 10 assumes the same outer diameter as the insulation 12 of the coiled conductor 14 of the pacing lead 20.

During the swaging process, the soft metal ball or wire 18 assumes an elongated shape as illustrated in FIG. 2. Teats 18a–18d are formed over the portions of the coiled conductor 14a–14c which assumed an elongated shape.

The mechanical joint resulting by the crimping and swaging referred to as a mechanical weld assumes mechanical and electrical connection of the soft metal member ball or wire 18 between the ring electrode 10 and the coiled conductor 14a, especially conductors 14a–14c as illustrated in FIG. 2.

The resultant product is a ring electrode 10 which has the same diameter as the insulation 12 of the pacing lead 20 and provides for a smooth outer surface for easy lead passage through veins and a lead introducer if utilized. The ring electrode 10 provides more flexibility in the area of the ring electrode 10, provides easy passage around curves, and has a tensile strength at the ring electrode substantially equal that of the insulation utilized over the pacing conductor.

Various modifications can be made to the ring electrode of the pacing lead of the present invention without departing from the apparent scope thereof. The ring electrode 10 can be utilized on any type of bipolar or unipolar lead as so desired.

Having thus described the invention, there is claimed as new and desired to be secured by Letters Patent:

1. Body implantable lead comprising:
    a coiled conductor having proximal and distal ends;
    an electrical connector coupled to said proximal end of said coiled conductor;
    a sheath of body compatible material having proximal and distal ends covering said coiled conductor having a hole slit intermediate said proximal and distal ends;
    means located within said hole means frictionally engaging said coiled conductor for electrically conducting to and from said coiled conductor; and
    an electrode covering said hole and said conducting means frictionally attached to said sheath and said conducting means.

2. Body implantable lead according to claim 1 wherein said electrode is a ring electrode being a hollow cylinder having an outside diameter approximately equal to that of said sheath.

3. Body implantable lead according to claims 1 or 2 wherein said electrically conducting means is a soft metal.

4. Body implantable lead according to claim 3 wherein said soft metal is silver.

5. Method of making a body implantable lead comprising the steps of:
    (a) slitting a hole in an insulating sheath having proximal and distal ends;
    (b) sliding said sheath over a coiled conductor;
    (c) placing a portion of soft metal within said hole;
    (d) sliding a hollow cylindrical ring electrode having an inside diameter greater than said sheath over said sheath to cover said portion of soft metal and said hole; and
    (e) swaging said hollow cylindrical ring electrode to an outside diameter approximately that of said sheath.

6. Method according to claim 5 wherein said soft metal is silver.

* * * * *